(12) United States Patent
Denizot et al.

(10) Patent No.: US 9,023,396 B2
(45) Date of Patent: May 5, 2015

(54) COMPOSITIONS BASED ON POLYSACCHARIDES GRAFTED BY POLYAMINE OR POLYSULPHURISED COMPOUNDS

(75) Inventors: Benoit Denizot, Bonneville (FR); Franck Lacoeuille, Angers (FR); Jean Jacques Le Jeune, Avrille (FR); Francois Hindre, Rennes (FR)

(73) Assignee: Laboratoires Cyclopharma, Saint Beauzire (FR)

( * ) Notice: Subject to any disclaimer, the term of this patent is extended or adjusted under 35 U.S.C. 154(b) by 503 days.

(21) Appl. No.: 12/670,811

(22) PCT Filed: Jul. 25, 2008

(86) PCT No.: PCT/EP2008/059825
§ 371 (c)(1),
(2), (4) Date: Jun. 18, 2010

(87) PCT Pub. No.: WO2009/013358
PCT Pub. Date: Jan. 29, 2009

(65) Prior Publication Data
US 2010/0254906 A1  Oct. 7, 2010

Related U.S. Application Data

(60) Provisional application No. 60/952,094, filed on Jul. 26, 2007.

(30) Foreign Application Priority Data

Jul. 26, 2007 (FR) ........................................ 07 56750

(51) Int. Cl.
*A61K 51/12* (2006.01)
*A61K 51/06* (2006.01)

(52) U.S. Cl.
CPC ............ *A61K 51/065* (2013.01); *A61K 51/1244* (2013.01)

(58) Field of Classification Search
None
See application file for complete search history.

(56) References Cited

U.S. PATENT DOCUMENTS

| 4,115,536 A | 9/1978 | Rothman et al. |
| 2005/0130932 A1* | 6/2005 | Norquist et al. ............... 514/54 |

FOREIGN PATENT DOCUMENTS

| CN | 1683377 | 10/2005 |
| JP | 20031044914 | 4/2003 |
| WO | 00/21571 | 4/2000 |
| WO | 02/41989 | 5/2002 |
| WO | 2006/088473 | 8/2006 |

OTHER PUBLICATIONS

Hosseinkhani et al., J Controlled Release 88(2), p. 297-312, 2003.*
Machine translation of JP2003-104914, original document published 2003.*
Elfstrand et al. Carbohydrate Polymers, 57, p. 389-400, 2004.*
(Continued)

*Primary Examiner* — Nissa Westerberg
(74) *Attorney, Agent, or Firm* — Thompson Coburn LLP

(57) ABSTRACT

New pharmaceutical compositions based on grafted polysaccharides and methods of preparing such compositions are provided. Methods of using the compositions in medical imaging—for example in scintigraphy and in internal radiotherapy—are also provided.

42 Claims, 11 Drawing Sheets

(56) References Cited

OTHER PUBLICATIONS

Elfstrand et al. Starch/Staerke 58, p. 381-390, 2006, first published online Jun. 29, 2006.*

Azzam et al., "Hydrophobized Dextran-Spermine Conjugate as Potential Vector for In Vitro Gene Transfection", Journal of Controlled Release, 2004, pp. 309-323, vol. 96.

Hosseinkhani et al., "Tumor Targeting of Gene Expression Through Metal-Coordinated Conjugation with Dextran", Journal of Controlled Release, 2003, pp. 297-312, vol. 88.

Lenucci et al, "Do Polyamines Contribute to Plant Cell Wall Assembly by Forming Amide Bonds with Pectins?", Phytochemistry, 2005, pp. 2581-2594, vol. 66.

Shaltiel et al, "Hydrophobic Chromatography: Use for Purification of Glycogen Synthetase", Proc. Nat. Acad. Sci. USA, Mar. 1973, pp. 778-781, vol. 70.

Eliyahu et al., "Relationships Between Chemical Composition, Physical Properties and Transfection Efficiency of Polysaccharide-Spermine Conjugates", Biomaterials, 2006, pp. 1646-1655, vol. 27.

* cited by examiner

COMPOSITIONS BASED ON POLYSACCHARIDES GRAFTED BY POLYAMINE OR POLYSULPHURISED COMPOUNDS

CROSS-REFERENCE TO RELATED APPLICATIONS

This application is a National Stage application of International Patent Application No. PCT/EP2008/059825, filed Jul. 25, 2008 and incorporated by reference herein in its entirety, which claims priority to U.S. Provisional Application 60/952,094 filed Jul. 26, 2007 and to French Application No. FR 07 56750 filed Jul. 26, 2007, both of which are incorporated by reference herein in their entireties.

The invention relates to new pharmaceutical compositions based on grafted polysaccharides and to the use thereof in medical imaging, specifically scintigraphy, and in internal radiotherapy.

Vector particles of radioactive elements have been used for a long time in the fields of medicine and biology (for a general overview, see Häfeli, 2001), for example for estimating tissue blood flow by means of non-resorbable microparticles of a sufficient size (several tens of micrometers) which are sequestered in the first capillary network encountered once they have been injected into the vascular network. Although said particles may be used, in the form of glass particles for example (Häfeli et al., 1999), to expose specific tissue (in particular tumour tissue) to ionising radiation, the fact that they are not resorbable means that it is not possible to develop routine in vivo applications therefor on a diagnostic level, and also frequently on a therapeutic level (when total ischaemia of the target tissue is not desirable).

The most common in vivo use of microparticles in humans is for scintigraphic diagnosis of a pulmonary embolism. This common disease (approximately 650,000 new cases annually in the USA) is caused by blood clots, most frequently from the lower limbs, which migrate through the venous system, pass through the right heart and block the pulmonary capillaries. If the embolism is massive there is a risk of heart pump failure. In order to be effective and to prevent large embolisms, it is necessary to detect small embolisms early in order to implement an extended anticoagulant treatment regime. X-ray spiral computed tomography (X-ray scanner) is a method which has become widespread in recent years, but its performance in terms of peripheral embolisms is poor. In addition, the dose of ionising radiation to which the chest is exposed is capable of causing breast cancer. Perfusion scintigraphy thus currently retains its place, ventilation being evaluated by aerosol or by radioactive gases.

Historically, one of the first uses of particles known to be resorbable was pulmonary perfusion scintigraphy using iron oxide particles labelled with $^{99m}$Tc (U.S. Pat. No. 3,962,412 and U.S. Pat. No. 4,057,616). This method, which used $Fe^{2+}$ iron ions, allowed a reduction in pertechnetate and a good level of bonding on the iron oxides and hydroxides, which formed the core of the particles, to be achieved. However, one of the limits of this type of technology was the difficulty in obtaining a homogeneous size of around several tens of micrometers. Furthermore, the process of lyophilising said preparations, which were to be used in the form of the labelling kit, was also delicate.

An alternative to the use of said particles is using proteins as particle matrices (U.S. Pat. No. 3,663,685), in particular egg albumin or serum albumin (U.S. Pat. No. 4,024,233). There are processes for obtaining homogeneous sizes (for example U.S. Pat. No. 6,709,650), often with a relatively high level of complexity in terms of production, which results in a significant level of inter-batch variability. In addition, labelling using iodine and technetium are relatively simple, proven processes (U.S. Pat. No. 4,410,507 for example). These products are currently widely used for diagnosing a pulmonary embolism in clinical practice. However, these particles have three significant limitations for use in humans, in particular in pulmonary perfusion scintigraphy after intravenous injection:

The in situ degradation kinetics frequently last for relatively long periods of time of more than four hours. This duration is less suitable than a shorter time period (from one to two hours) in terms of intravenous treatment with fibrinolytics, allowing early diagnosis and allowing the effectiveness to be checked subsequently, directly after treatment;

These particles may be immunogens, and this is why proteins of human origin are preferably used;

Whether these particles are of human or animal origin, all of these formulations potentially carry the risk of transmitting contagions, in particular viral contagions (HIV, hepatitis, etc.) and prions (unconventional transmissible agents which are responsible for Kreutzfeld-Jacob disease, etc.) and this transmission is currently very difficult to prevent. One method of increasing safety is to only prepare the particles with albumin solutions which have been stored for six months. In addition to the additional costs involved, this precaution is not wholly reliable since one of the blood donors may be subject to seroconversion or may subsequently declare the disease and thus may be found to be a carrier (and potentially a contaminant) after a silent incubation phase of several years (in the case of unconventional transmissible agents).

Certain teams have proposed the use of liposomes, having the specific advantage of being non-toxic. However, producing large liposomes (several tens of micrometers) which are stable during lyophilisation and reconstitution is extremely difficult. Furthermore, there are three broad processes for labelling liposomes: incorporating the radioactive product in the interior of the vesicle (during preparation or with a lipophilic product which becomes hydrophilic in the interior, such as l'HMPAO-$^{99m}$Tc), using the aliphatic core of the lipid bilayer as a retention system of a hydrophobic product (such as $^{111}$In-oxine), or surface-grafting complexing agents as in the case of l'HYNIC-$^{99m}$Tc. In all of the above cases, achieving a good degree of labelling is difficult due to the instability of the liposomes.

In order to bypass these limitations, it was proposed that completely synthetic biodegradeable polymers be used (ES 2096521, Delgado A. et al., 2000). However, in the opinion even of the authors themselves, using polyesters makes it difficult to achieve stable labelling and a good level of reproducibility for lyophilisation and the release kinetics.

A complementary way of obtaining beneficial polymers and particles is to use natural or artificial polysaccharides (U.S. Pat. No. 3,663,685, U.S. Pat. No. 3,758,678). The vegetable or microbiological origins of some of said polysaccharides ensure that there can be no transmission of pathogens from the animal kingdom. In addition to the ease with which they can be produced and the low cost (of a number of them), the rich chemistry thereof allows their biodegradation process to be well controlled.

The patent application FR 2 273 516 thus discloses the use of amylopectin microcarrier beads which are cross-linked by epichlorohydrin and are labelled by $^{99m}$Tc for pulmonary perfusion scintigraphy. However, amylopectin hydroxyl groups form weak bonds with technetium and do not allow stable labelling to be achieved. Furthermore, epichlorohydrin, which was used for cross-linking, is known to be highly toxic and mutagenic.

Starch particles grafted by radioactive elements by way of amine complexing systems comprising at least one sulphur atom have also been disclosed (FR 2 797 769). The rate of complexation of the radioactive elements by the complexing groups seems to be relatively satisfactory, but specific formulations described exhibit very rapid degradation kinetics (less than 10 minutes), which is a limiting factor in terms of tomography. The degradation kinetics appear to be dependant in part on the oxidation rate and the grafting rate of the cornstarch selected. Moreover, they appear to have limited storage stability. Finally, the complexing groups described in this document are relatively complex structures which may require several stages of chemical synthesis, which may increase the risk of toxicity of the radiopharmaceutical compositions and the production costs thereof. On a toxicological level, the metabolic pathways for the degradation of the compounds studied have not been identified and may be sources of potentially dangerous secondary compounds.

More generally, the polysaccharide polymers on which the radioactive atoms have been fixed were used as radioactive labelling agents (dextran labelled with $^{99m}$Tc) for the vascular and/or interstitial zones (as a function of the molecular weight of dextran, Kellaway I. W., et al., 1995), as a permeability indicator (Akgun A. et al., 2005) or for detecting the sentinel node (Paiva G. R. et al., 2006), as an agent allowing the quantity of radioactive atoms to be increased in internal radiotherapy uses (dextran iodised with $^{131}$I coupled to proteins, Andersson A. et al., 1992) and even as an agent allowing the renal clearance of the radioactive tracer to be increased in order to increase the signal-noise ratio in uses for active vectorisation by peptides or antibodies (dextran labelled with $^{99m}$Tc, Line B. R., et al., 2000).

According to a first object, the invention relates to compositions comprising a polysaccharide having one or more complexing groups of formula (I) or (II) covalently bound to said polysaccharide:

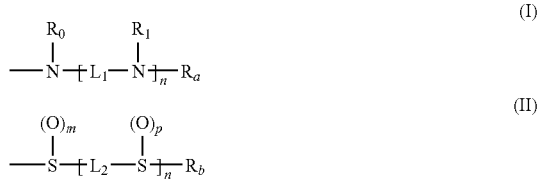

in which formulae (I) and (II):

$R_0$ represents a hydrogen atom or a $C_1$-$C_6$ alkyl group;

$R_1$, $R_a$, which are the same or different, represent a hydrogen atom, a linear or branched $C_1$-$C_6$ alkyl group, and are optionally substituted in the same or a different manner by one or more halogen atoms (fluorine, chlorine, bromine, iodine), alkyl, alkenyl, oxo, —C(=O)OR$_0$, —C(=O)R$_0$, nitro, cyano, hydroxyl, alkoxy, amino, alkyl($C_1$-$C_6$)amino, dialkyl ($C_1$-$C_6$)amino, phosphine, phosphate, phosphonate, diphosphonate groups, or a non-sulphurised peptide radical, or $R_1$, $R_a$, the same or different, represent —C(=O)OR$_0$, —C(=O)R$_0$, an oxime group, a non-sulphurised peptide radical, a phosphonate group or a diphosphonate group;

$R_b$ represents a hydrogen atom, a linear or branched $C_1$-$C_6$ alkyl group, which are optionally substituted in the same or a different manner by one or more halogen atoms (fluorine, chlorine, bromine, iodine), alkyl, alkenyl, oxo, C(=O)OR$_0$, —C(=O)R$_0$, hydroxyl, alkoxy, thio, alkylthio, phosphine, phosphate, phosphonate, diphosphonate groups, or a peptide radical, or $R_b$ represents —C(=O)OR$_0$, —C(=O)R$_0$, an oxime group, a peptide radical, a phosphonate group or a diphosphonate group;

$L_1$ represents a linear or branched $C_1$-$C_6$alkylene group, a linear or branched $C_2$-$C_6$ alkenylene group, an arylene or bisarylene group, said groups $L_1$ being capable of being the same or different for n>1, optionally interrupted by one or more oxygen atoms, and capable of being substituted in the same or a different manner for n>1 by one or more halogen atoms (fluorine, chlorine, bromine, iodine), alkyl, alkenyl, oxo, —C(=O)OR$_0$, —C(=O)R$_0$, nitro, cyano, hydroxyl, alkoxy, amino, alkyl($C_1$-$C_6$)amino, dialkyl($C_1$-$C_6$)amino, phosphine, phosphate, phosphonate, diphosphonate groups, or a non-sulphurised peptide radical;

$L_2$ represents a linear or branched $C_1$-$C_6$ alkylene group, a linear or branched $C_2$-$C_6$ alkenylene group, an arylene or bisarylene group, said groups $L_2$ being capable of being the same or different for n>1, optionally interrupted by one or more oxygen and/or sulphur atoms, and capable of being substituted in the same or a different manner for n>1 by one or more halogen atoms (fluorine, chlorine, bromine, iodine), alkyl, alkenyl, oxo, —C(=O)OR$_0$, —C(=O)R$_0$, hydroxyl, alkoxy, thio, alkylthio, phosphine, phosphate, phosphonate, diphosphonate groups, or a peptide radical;

n is an integer between 1 and 6 and m and p are the same or different and may be 0, 1 or 2, m and p each preferably representing 0, all or part of said groups of formula (I) or (II) forming a complex with at least one polyvalent metal.

These compositions are particularly advantageous in that they allow an elevated rate of complexation of said polyvalent atoms to be achieved, and this allows the doses of radiopharmaceutical compositions administered to a patient in terms of the radioactive atoms to be reduced, the quality of the image in the medical imaging process to be improved and the toxological risk to be reduced.

In addition, these compositions have very good pulmonary collection, are not toxic at the doses used, are readily biodegradable by known methods of bioelimination, sterilisable and may be packaged in the form of a diagnostic case.

The polysaccharide according to the invention is preferably in the form of preferably spherical particles, in particular microparticles or nanoparticles.

The particle size may be between 10 nm and 200 µm, preferably between 10 and 100 µm, and more preferably about 40 µm for capillary blocking applications (such as pulmonary perfusion scintigraphy, for example for scintigraphic diagnosis of pulmonary embolism). The nanometric particles, i.e. those having a size of less than 1 µm (in particular those having a size of between 10 and 500 nm, specifically those having a size of approximately 40 to 80 nm), are particularly useful for the administration of the compositions according to the invention intratissularly, for example to detect the presence of and/or to visualise sentinel ganglions, for lymphoscintigraphy, for producing imaging of the bone marrow or the lymphatic ganglions after intravenous injection ("marked colloid scintigraphy") or else for the irradiation of tissues by said polysaccharides in internal radiotherapy.

The micrometric particles, i.e. those having a size of about 1 µm and greater (up to about 10 µm), can be administered intravenously and are particularly useful for visualising by medical imaging the mononucleate phagocyte system such as the liver, the bone marrow or else for treating hepatic or splenic tumours by internal radiotherapy.

The polysaccharide which can be used according to the invention is preferably of natural origin, in particular of vegetable or microbiological origin. Examples include, in particular, starch, cellulose, amylopectin, amylose, agarose, pullalan, chitosan or dextran and derivatives thereof as well mixtures of two or more thereof; starch is particularly preferred.

Advantageously, the polysaccharide reduces the microbiological risks of the radiopharmaceutical compositions in comparison with those based on proteins such as human albumin and gelatin, generally porcine gelatin. A further advantage is that the degradation kinetics in situ can be modified according to the rate of oxidation or grafting of the polysaccharide, this being difficult to achieve in a reproducible manner with proteins.

The starch may be, for example, corn, wheat, rice, potato or millet starch, etc. or a derivative such as hydroxyethylamidone (HES) which degrades slowly after intravenous injection, enabling it to be used as a vessel-filling solution in the case of hypovolemic shock. This product does not activate complement and thus does not lead to the resulting secondary effects.

Preferably, the complexing groups are groups of formula (I) in which $R_1$ and/or $R_a$ represent a hydrogen atom.

Preferably, n is 1, 2 or 3.

Preferably, at least one of the values m or p represents 0, or m and p each represent 0.

Preferably, $L_1$ is an alkylene group, in particular a $C_2$-$C_5$ alkylene group.

Examples of particularly preferred complexing groups of formula (I) include in particular those obtained by covalent bonding of putrescine $NH_2(CH_2)_4NH_2$, spermine $H_2N(CH_2)_3NH(CH_2)_4NH(CH_2)_3NH_2$, spermidine $NH_2(CH_2)_3NH(CH_2)_4NH_2$, or cadaverine $NH_2(CH_2)_5NH_2$, with the oxidised polysaccharide.

These complexing groups are particularly advantageous as they are derived from biogenic polyamines, i.e. those present in a biological medium, and this reduces the risk of toxicity of the compositions because the methods of degradation of these products are well known. In addition, these endogenous polyamines are commercially available at low cost.

The proportion of complexing groups can be from 0.1 to 200%, based on the monosaccharide units of the polysaccharide, preferably from 10 to 100%.

The polyvalent metal present in the compositions can be selected from the metallic elements having an atomic number of between 20 and 33, between 38 and 51, between 56 and 84 or between 88 and 103.

Non-limiting examples of polyvalent metals include the radioactive isotopes of technetium such as $^{99m}Tc$, $^{94}Tc$ or $^{94m}Tc$, those of rhenium such as $^{188}Re$ or $^{186}Re$, those of copper such as $^{60}Cu$, $^{61}Cu$, $^{64}Cu$ or $^{67}Cu$, those of strontium such as $^{89}Sr$, those of indium such as $^{111}In$ or $^{113}In$, those of samarium such as $^{153}Sm$, those of tin such as $^{113m}Sn$, those of scandium such as $^{44}Sc$, those of yttrium such as $^{90}Y$ or $^{86}Y$, those of gallium such as $^{67}Ga$ or $^{68}Ga$, those of gadolinium or those of lutetium, $^{99m}Tc$ being particularly preferred.

Preferably, the compositions according to the invention also comprise a pharmaceutically acceptable vehicle or excipient.

Preferably, said composition contains an effective amount of polysaccharide marked by a radioactive element via the complexing groups of formula (I) or (II) according to the invention.

The compositions according to the invention are preferably pharmaceutical and/or diagnostic compositions.

The pharmaceutical compositions according to the invention can be presented in forms intended for parenteral, intravenous, intra-arterial, intramuscular, interstitial, intracerebral, intrathecal or intra-pulmonary administration, for administration via the ORL sphere, ocular, vaginal or rectal mucous membranes or even enterally (gastric transit) and via aerosols.

They will therefore be presented in the form of solutes, solutions or injectable suspensions or in the form of single or multiple dose powders or vials.

For parenteral use, water, aqueous solutions, physiological serum and isotonic solutions are the most convenient vehicles to use.

The compositions according to the invention may be prepared by application or adaptation of any method known per se and/or within the scope of one skilled in the art, in particular those described by Larock in *Comprehensive Organic Transformations*, VCH Pub., 1989, or by application or adaptation of the processes described in the following examples.

According to a further object, the invention therefore also relates to a process for preparing compositions according to the invention comprising the steps of:
 i) bringing a polysaccharide into contact with a controlled oxidising agent;
 ii) bringing the oxidised polysaccharide into contact with a compound of formula (Ia) or (IIa):

in which $L_1$, $L_2$, $R_0$, $R_1$, $R_a$, $R_b$, m, n and p are as defined above, to obtain a polysaccharide comprising complexing groups of formula (I) or (II) covalently bound to said polysaccharide;
 iii) optionally, bringing the polysaccharide obtained into contact with a reducing agent;
 iv) bringing the polysaccharide obtained into contact with a polyvalent metal salt.

The process according to the invention is generally carried out in water, at ambient temperature.

Examples of controlled oxidising agents that can be used include, in particular, the periodates, for example sodium periodate.

Examples of reducing agents include, in particular, sodium borohydride.

Without willing to be bound to any particular theory, the controlled oxidation of the polysaccharide leads to the formation of carbonyl functions, which react with the HN— or HS— groups of compounds of formula (Ia) or (IIa) respectively.

As an example, the starch, after controlled oxidation, leads to the formation of aldehyde functions which can react with the $H_2N$— groups of putrescine, spermine, spermidine or cadaverine to form, notably after reduction, imine covalent bonds (—CH=N—).

Step iv) of bringing the polysaccharide obtained into contact with a polyvalent metal salt (marking reaction) can be carried out, and in the case of marking is advantageously carried out with $^{99m}$Tc, in the presence of reducing agents of the tin, borate and derivatives or ascorbic acid type, or any other means which effectively reduce the radioactive polyvalent metal salt, in particular in the case of technetium.

The derivatives of formula (Ia) or (IIa) in which $L_1$, $L_2$, $R_0$, $R_1$, $R_a$, $R_b$, m, n and p have the same meaning as in formula (I) or (II) above are either commercially available or prepared on the basis of methods described in the literature.

The process according to the invention can also comprise the subsequent step of isolation of the compositions obtained.

According to a further object, the invention relates to the use of the above defined compositions, in particular for producing a diagnostic composition for medical, human or veterinary imaging, in particular monophotonic, biphotonic or even polyphotonic scintigraphic imaging.

The compositions according to the invention are also particularly useful for visualising one or more organs in a patient or an animal, such as the lung, the liver, the spleen, bone marrow or lymph nodes.

Some compositions according to the invention may also be used for visualising sentinel nodes.

According to a further object, the compositions according to the invention may be used for producing a pharmaceutical composition for treating cancer in a patient or an animal by means of internal radiotherapy, in particular for treating lymph nodes or hepatic or splenic tumours.

In this context, the compositions of the invention are generally used to expose cancerous tumours, in particular of the liver and/or the spleen, or lymphatic nodes, to ionising radiation.

According to a further object, the invention relates to polysaccharides comprising one or more complexing groups of formula (I) or (II) covalently bound to said polysaccharides, said polysaccharides being as defined above.

These polysaccharides are in fact particularly useful for producing the compositions according to the invention.

The invention also relates to polysaccharides comprising one or more complexing groups of formula (I) or (II) covalently bound to said polysaccharides, obtainable according to steps i) to iii) of the process as defined above.

As used above and in the entire description of the invention, the terms, unless stated otherwise, should be understood as having the following meanings:

The term "polysaccharide" denotes a polymer resulting from the linkage of a plurality of monosaccharide units, in particular of 10 to 1000 monosaccharides.

According to the present invention, the alkyl radicals are straight chain or branched saturated hydrocarbon radicals, containing from 1 to 6 carbon atoms, preferably from 1 to 4 carbon atoms.

Linear radicals include the methyl, ethyl, propyl, butyl, pentyl and hexyl radicals.

The isopropyl, tert-butyl, 2-ethylhexyl, 2-methylbutyl, 2-methylpentyl and 1-methylpentyl radicals can be mentioned in particular as branched radicals or radicals substituted by one or more alkyl radicals.

Alkoxy radicals according to the present invention are radicals of formula —O-alkyl, the alkyl being as defined hereinbefore.

The alkylthio radicals according to the present invention are radicals of formula —S-alkyl, the alkyl being as defined hereinbefore.

The alkylene radicals are branched or linear divalent hydrocarbon radicals containing from 1 to 6 carbon atoms.

The alkenylene radicals are straight-chain or linear divalent hydrocarbon radicals and comprise one or more ethylene unsaturations. The alkenylene radicals include, in particular, the —CH=CH—, —CH$_2$CH=CH—, —C(CH$_3$)=CH—, —CH$_2$CH=CHCH$_2$-radicals.

Arylene denotes a divalent monocyclic or bicyclic aromatic hydrocarbon radical containing from 6 to 10 carbon atoms. The arylene radicals include in particular the phenylene or naphthylene radical.

Bis-arylene denotes a divalent system comprising two monocyclic or bicyclic aromatic hydrocarbon radicals containing from 6 to 10 carbon atoms. The bis-arylene radicals include in particular the biphenylene or binaphthylene radical.

Figure 1:
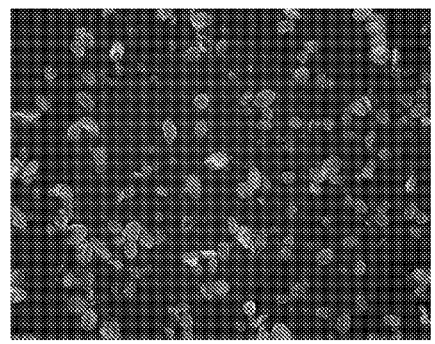
FIG. 1: Coupling of cadaverine to starch particles viewed with an optical fluorescence microscope in the presence of fluorescamine.

Different urinary samples collected were eluted using a Sephadex G15 column with an exclusion limit of 1,500 daltons (18), using a P6 column with an exclusion limit of 5,000 daltons (19) and using a Sephadex G50 with an exclusion limit of 10,000 daltons (20).

The following examples illustrate the invention but are not limiting. The starting materials used are products which are either known or prepared in accordance with known methods.

EXAMPLES

No. 1

Starch Particles Coupled to a Natural Polyamine: Verification of Coupling by Means of Reaction with Fluorescamine Controlled Oxidation of Starch Particles:

10 g (corresponding to 0.055 moles of glucose unit) of potato starch (native potato starch in accordance with the monograph of the European pharmacopoeia) sieved between 36 and 50 µm were dispersed in 100 ml water. 0.028 moles of sodium periodate ($NaIO_4$), i.e. 6 g, previously dissolved in 100 ml water were added. The suspension was stirred for 18 hours at ambient temperature. After 18 hours, a particle suspension of 50% oxidised starch was obtained. The oxidised starch was collected by means of centrifugation then rinsed three times with 200 ml water.

Functionalisation of the Oxidised Starch by Coupling to a Natural Polyamine:

After rinsing, 1 g starch, i.e. 0.0055 moles of glucose unit, was incubated in 60 ml water and contacted with a solution of 0.00385 moles of natural polyamine (putrescine, cadaverine, spermine or spermidine) in 10 ml water, i.e. 0.0077 moles of $NH_2$ (1.4 eq), for 18 hours at ambient temperature. In order to stabilise the imine formed, 0.56 g $NaBH_4$, i.e. 0.015 moles, were added to the modified starch suspension under stirring for 1 hour. The particles were then decanted, filtered and washed three times with 200 ml water then lyophilised.

Verification of Starch-Amine Coupling by Means of Optical Fluorescence Microscopy:

The coupling of the cadaverine to starch particles was verified by viewing, by way of optical fluorescence microscopy, a fluorescent complex formed during the addition of 100 µl of a 3 mg per ml fluorescamine ($C_{17}H_{10}O_4$) solution to starch particles functionalised with cadaverine (10 mg in 300 µl water). The formation of this fluorescent complex, verified by fluorescence microscopy, indicates the presence of primary amine functions ($NH_2$) on the functionalised starch particles with a specific reaction of said amines on the clear fluorescamine which then turns a greenish yellow colour, confirming the efficacy of the starch/oxidised amine coupling.

No. 2

Oxidised Potato Starch Particles as a Radio Tracer Used for Scintigraphic Imaging of the Liver and the Spleen Controlled Oxidation of Starch Particles:

As in example 1, 10 g (corresponding to 0.055 moles of glucose unit) of potato starch (native potato starch in accordance with the monograph of the European pharmacopoeia) sieved between 36 and 50 µm were dispersed in 100 ml water. 0.0112 moles of sodium periodate ($NaIO_4$), i.e. 2.4 g, previously dissolved in 100 ml water was added to the particle suspension. The suspension was stirred for 18 hours at ambient temperature. After 18 hours, a particle suspension of 20% oxidised starch was obtained. The oxidised starch was collected by means of centrifugation, rinsed three times in 200 ml water and then lyophilised.

Reaction of Labelling with $^{99m}Tc$:

20 mg of 20% oxidised and lyophilised starch were placed in an empty elution flask under inert atmosphere. 4 ml of physiological serum then 20 µg of $SnCl_2$, $2H_2O$ were added. 1 ml of a 185 MBq/ml sodium pertechnetate solution ($Na^{+99m}TcO_4^-$) was added. The solution was stirred for 1 minute and the radiochemical purity (RCP) was checked by filtering 1 ml of the solution on a 0.22 µm filter and rinsing the filter with 5 ml physiological serum.

The radiochemical purity corresponds to:

RCP=(Activity on the filter/Total activity)×100;

In example 2, it is greater than 99%.

Figure 2:
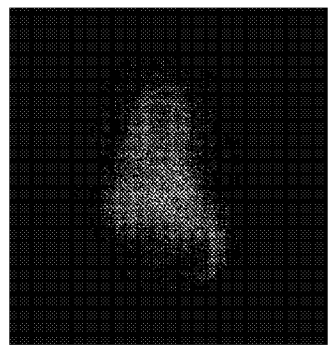
FIGS. 2 and 3: Scintigraphic images typical of rats (anterior projection) having intravenously received 20% oxidised starch particles labelled with 4 MBq of $^{99m}$Tc just after injection (FIG. 2) and after 15 minutes (FIG. 3).
Figure 3:
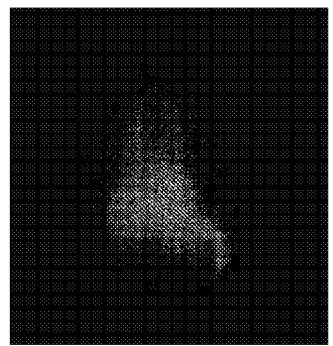

Scintigraphic Visualisation of the Biodistribution after Intravenous Injection in Rats:

After labelling, 4 MBq of 20% oxidised starch particles labelled with $^{99m}Tc$ were injected intravenously (penile vein) in male Wistar rats weighing approximately 200 g. A scintigraphic acquisition of 30 kCps was carried out immediately after injection and then 15 minutes later. After a visualisation phase of the lungs (upper region), the liver and the spleen (lower right-hand region), the activity was quickly (within 15 minutes) concentrated in the liver and the spleen (fixed point in the lower right-hand region of the image) (FIGS. 2 and 3).

No. 3

Oxidised Potato Starch Particles Coupled to Cadaverine as a Radio Tracer Used for Scintigraphic Imaging of Lung Perfusion Controlled Oxidation of Starch Particles:

10 g (corresponding to 0.055 moles of glucose unit) of potato starch (native potato starch in accordance with the monograph of the European pharmacopoeia) sieved between 36 and 50 µm were dispersed in 100 ml water. 0.028 moles of sodium periodate ($NaIO_4$), i.e. 6 g, previously dissolved in 100 ml water were added. The suspension was stirred for 18 hours at ambient temperature. After 18 hours, a particle suspension of 50% oxidised starch was obtained. The oxidised starch was collected by means of centrifugation then rinsed three times with 200 ml water.

Functionalisation of Oxidised Starch by Coupling to Cadaverine:

10 g oxidised starch, i.e. 0.055 moles of glucose unit, were incubated in 600 ml water and contacted with 4 g cadaverine ($NH_2(CH_2)_5NH_2$) dissolved in 100 ml water, i.e. 0.0385 moles of cadaverine, i.e. 0.077 moles of $NH_2$ (1.4 eq) for 18 hours at ambient temperature. In order to stabilise the imine formed, 5.6 g $NaBH_4$, i.e. 0.15 moles, were added to the modified starch suspension under stirring for 1 hour. The particles were then decanted, filtered and washed three times with 200 ml water, then lyophilised.

Reaction of Labelling with $^{99m}Tc$:

20 mg starch coupled to cadaverine and lyophilised were placed in an elution flask under inert atmosphere. 4 ml of physiological serum then 60 µg of $SnCl_2$, $2H_2O$ were added. 1 ml of a 185 MBq/ml sodium pertechnetate solution ($Na^{+99m}TcO_4^-$) was added. The solution was stirred for 1 minute and the radiochemical purity (RCP) was checked by filtering 1 ml of the solution on a 0.22 µm filter and rinsing the filter with 5 ml physiological serum.

The radiochemical purity corresponds to:

RCP=(Activity on the filter/Total activity)×100;

In example 3, it is greater than 95%.

Figure 4:
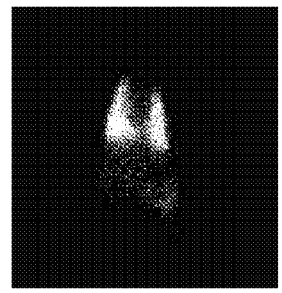
FIGS. 4, 5, 6: Scintigraphic images typical of rats (anterior projection) having intravenously received 50% oxidised starch particles coupled to cadaverine labelled with 4 MBq of $^{99m}$Tc after 15 minutes (FIG. 4), 30 minutes (FIG. 5) and 90 minutes after injection (FIG. 6).
Figure 5:
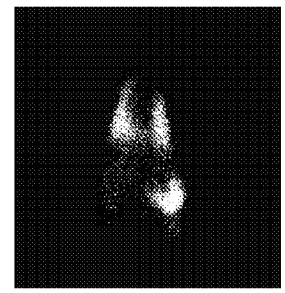
Figure 6:
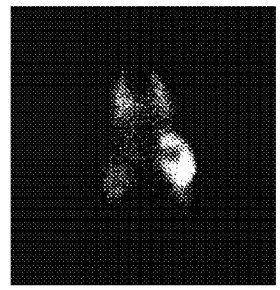

Scintigraphic Visualisation of the Biodistribution after Intravenous Injection in Rats:

After labelling, 4 MBq 50% oxidised starch particles coupled to cadaverine labelled with $^{99m}$Tc were intravenously injected (penile vein) in male Wistar rats weighing approximately 200 g. A scintigraphic acquisition of 30 kCps was carried out immediately after injection, at 15 minutes, 30 minutes and then 90 minutes later (FIGS. 4 to 5). After an exclusive visualisation phase of the lungs, activity of the spleen and then the kidneys increased rapidly with a marked decrease in lung activity after 90 minutes. In FIGS. 4 to 6, the significant absence of activity in the liver, whatever the time of analysis, should be noted. Likewise, good visibility on the initial image of the lungs and the almost complete absence of visualisation of the liver and the spleen are also noted. At 30 minutes, the spleen and the start of fixation of the kidneys can be seen, these two elements increasing substantially at 90 minutes with a marked decrease in lung activity.

No. 4

Oxidised Potato Starch Particles Coupled to Cadaverine as a Radio Tracer without Use of Metal Reducers ($SnCl_2$) for Scintigraphic Imaging of Lung Perfusion Controlled Oxidation of Starch Particles:

10 g (corresponding to 0.055 moles of glucose unit) of potato starch (native potato starch in accordance with the monograph of the European pharmacopoeia) sieved between 36 and 50 μm were dispersed in 100 ml water. 0.028 moles of sodium periodate ($NaIO_4$), i.e. 6 g, previously dissolved in 100 ml water were added. The suspension was stirred for 18 hours at ambient temperature. After 18 hours, a particle suspension of 50% oxidised starch was obtained. The oxidised starch was collected by means of centrifugation then rinsed three times with 200 ml water.

Functionalisation of the Oxidised Starch by Coupling to Cadaverine:

10 g oxidised starch, i.e. 0.055 moles of glucose unit, were incubated in 600 ml water and contacted with 4 g cadaverine ($NH_2(CH_2)_5NH_2$) dissolved in 100 ml water, i.e. 0.0385 moles of putrescine, i.e. 0.077 moles of $NH_2$ (1.4 eq) for 18 hours at ambient temperature. In order to stabilise the imine formed, 5.6 g $NaBH_4$, i.e. 0.15 moles, were added to the modified starch suspension under stirring for 1 hour. The particles were then decanted, filtered and washed three times with 200 ml water, then lyophilised.

Reaction of Labelling with $^{99m}$Tc without Use of a Reducing Agent:

1 ml of a 185 MBq/ml sodium pertechnetate ($Na^{+99m}TcO_4^-$) solution was placed in an Isolink™ flask containing the following mixture in lyophilised form: 8.5 mg sodium tartrate, 2.85 mg sodium tetraborate, 7.15 mg sodium carbonate and 4.5 mg sodium boranocarbonate. The flask was placed in a dry water bath at 100° C. for 20 minutes. The solution obtained was neutralised by adding 1 ml of a 0.1 N hydrochloric acid (HCl) solution. After neutralisation, the solution was placed in a flask under inert atmosphere containing 20 mg of oxidised starch coupled to cadaverine.

The suspension was stirred for 15 minutes and the radiochemical purity (RCP) was checked by filtering 1 ml of the solution on a 0.22 μm filter and rinsing the filter with 5 ml physiological serum.

The radiochemical purity corresponds to:

RCP=(Activity on the filter/Total activity)×100;

In example 4, it is greater than 95%.

Figure 7:
FIGS. 7, 8, 9: Scintigraphic images typical of rats (anterior projection) having intravenously received 50% oxidised starch particles coupled to cadaverine labelled with 4 MBq of $^{99m}$Tc after 5 minutes (FIG. 7), 15 minutes (FIG. 8) and 30 minutes after injection (FIG. 9).
Figure 8:
Figure 9:
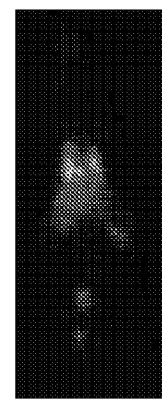

Scintigraphic Visualisation of the Biodistribution after Intravenous Injection in Rats:

After labelling, 4 MBq 50% oxidised starch particles coupled to cadaverine labelled with $^{99m}$Tc were intravenously injected (penile vein) in male Wistar rats weighing approximately 200 g. Continuous dynamic scintigraphic acquisition over 90 minutes at 30-second intervals was carried out immediately after injection (FIGS. 7 to 9). After 5 minutes (FIG. 7), almost exclusive visualisation of the lungs and low hepatic and renal activity were observed. Stable lung activity was observed at 15 minutes (FIG. 8) and 30 minutes (FIG. 9) after injection. In FIGS. 7 to 9, the absence of significant activity in the spleen, whatever the time of analysis, should be noted. Likewise, no increase in hepatic and renal activity is observed during the time period (FIGS. 8 and 9) which is explained by the high level of stability of lung capture.

No. 5

Coupling of Oxidised Starch Microparticles with Natural Polyamines

Figure 10:
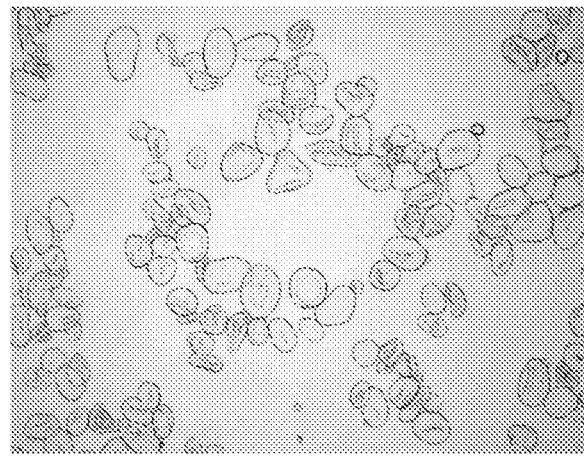
FIGS. 10 and 11: Morphological characteristics viewed by optical microscopy (at 10× magnification) of 50% oxidised starch microparticles labelled before (FIG. 10) and after reaction with cadaverine (FIG. 11).
Figure 11:
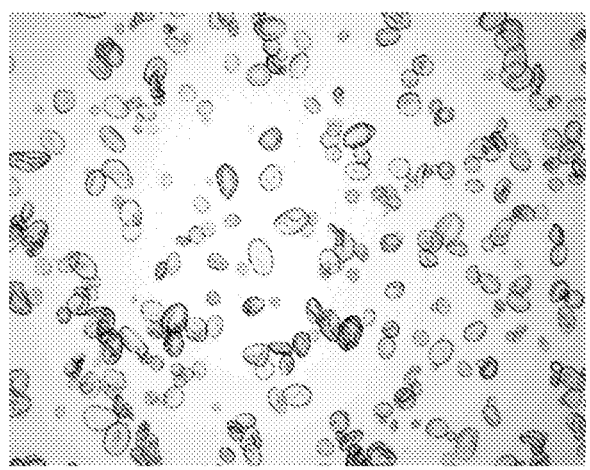
Figure 12:
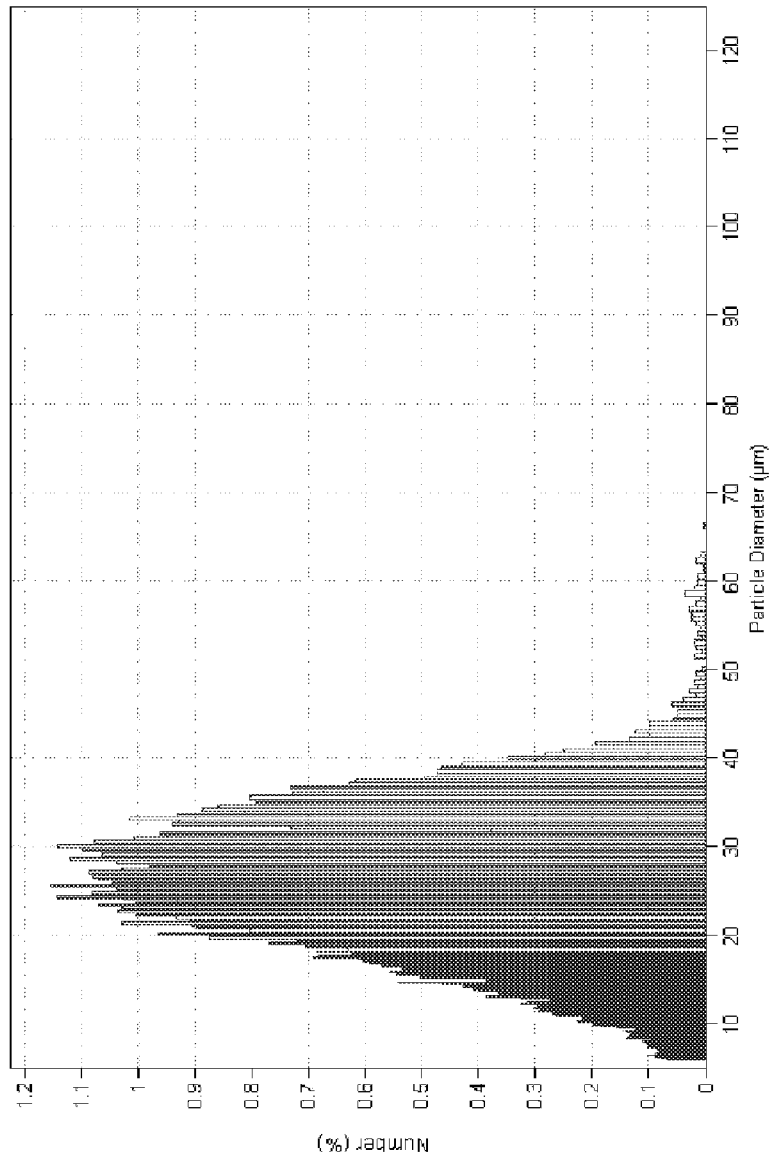
FIG. 12: Example of size distributions of oxidised starch microparticles coupled to cadaverine measured using a Coulter Multisizer 3 counter.

50% periodate oxidised potato starch particles prepared in accordance with example 1 were incubated (18 hours at ambient temperature) in the presence of cadaverine. After morphological analysis by means of optical microscopy (FIGS. 10 and 11) and granulometric microscopy using a Coulter Multisizer™ counter (FIG. 12), the particles coupled to cadaverine appeared to be rather homogeneous in terms in terms of morphology (FIG. 11) and in terms of size distribution (FIG. 12).

It is important to choose a homogeneous particle-size distribution in order to increase the proportion of particles blocked at pulmonary capillaries, with an optimum of approximately 20 to 40 μm. Below 10 μm, the particles run the risk of not being correctly stopped at the lung and being captured by the system of mononucleated phagocytes, in particular at the liver and the spleen.

No. 6

Optimising Preparation of Particles Coupled to Cadaverine and Preparation of Formulations A, B, C In order to optimise microparticle preparations, a plurality of experiment plans were established in order to determine the optimum parameters of the reaction for coupling oxidised starch to cadaverine. A first experiment plan made it possible to reveal the factors which influence or do not influence the coupling reaction. A second experiment plan made it possible to quantitatively determine the influence of the experimental parameters and to thus obtain the reaction conditions best suited to the production of microparticles able to effectively complex $^{99m}$Tc.

Figure 13:
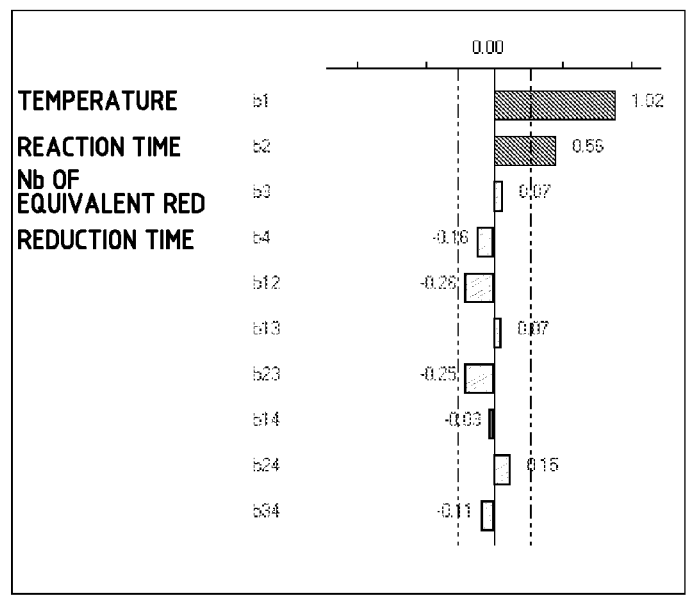
FIG. 13: Graphic study of the effects of temperature (B1), reaction time (B2), reducing agent equivalent value (B3) and lastly reduction time (B4) on the percentage of nitrogen contained in the final microparticles.

The first experiment plan made it possible, based on 14 experiments (Table 1), to determine the qualitative influence of 4 experimental variables (B1: reaction temperature; B2: reaction time; B3: reducing agent equivalent value; B4: reduction time). Each of the experimental variables was tested at 2 levels, one low and one high. In all the experiments, the response was evaluated by measuring the percentage of nitrogen contained in the final microparticles (main judging point measured by elementary analysis), the yields of the coupling reaction and the granulometric distribution of the microparticles obtained (Coulter Multisizer™ counter). The results obtained (FIG. 13) indicate the weak influence or lack of influence of particular reaction parameters (B3: reducing agent equivalent value; B4; reduction time) on the nitrogen content in the final microparticles and, in contrast, the rather positive and significant influence of temperature and reaction time thereon. The increase in the temperature and reaction time thus allows coupling of the cadaverine to oxidised starch microparticles to be increased and is thus more favourable to another complexation of $^{99m}$Tc by the microparticles.

TABLE 1

Experiment plan no. 1, studying the qualitative influence of 4 factors (B1, B2, B3 and B4) on the response in size and percentage of nitrogen in the starch microparticles at the end of the coupling reaction.

| Exp no. | B1 | B2 | B3 | B4 | Average size (μm) | % particles <10 μm | % nitrogen |
|---|---|---|---|---|---|---|---|
| 1 | 25 | 4 | 1 | 15 | 30 | 12 | 7.67 |
| 2 | 25 | 18 | 10 | 60 | 18 | 23 | 9.10 |
| 3 | 40 | 4 | 10 | 60 | 28 | 15 | 10.30 |
| 4 | 40 | 18 | 1 | 60 | 28 | 13 | 11.14 |
| 5 | 40 | 18 | 10 | 15 | 24 | 19 | 11.00 |
| 6 | 40 | 18 | 1 | 15 | 21 | 16 | 11.00 |
| 7 | 40 | 4 | 10 | 15 | 30 | 12 | 11.20 |
| 8 | 40 | 4 | 1 | 60 | 26 | 12 | 9.74 |
| 9 | 25 | 18 | 10 | 15 | 23 | 14 | 9.28 |
| 10 | 25 | 18 | 1 | 60 | 19 | 22 | 9.41 |
| 11 | 25 | 18 | 1 | 60 | 21 | 15 | 9.94 |
| 12 | 25 | 18 | 1 | 60 | 25 | 9 | 9.92 |
| 13 | 25 | 18 | 1 | 60 | 19 | 20 | 10.02 |
| 14 | 25 | 4 | 10 | 60 | 30 | 8 | 7.66 |

Figure 14:
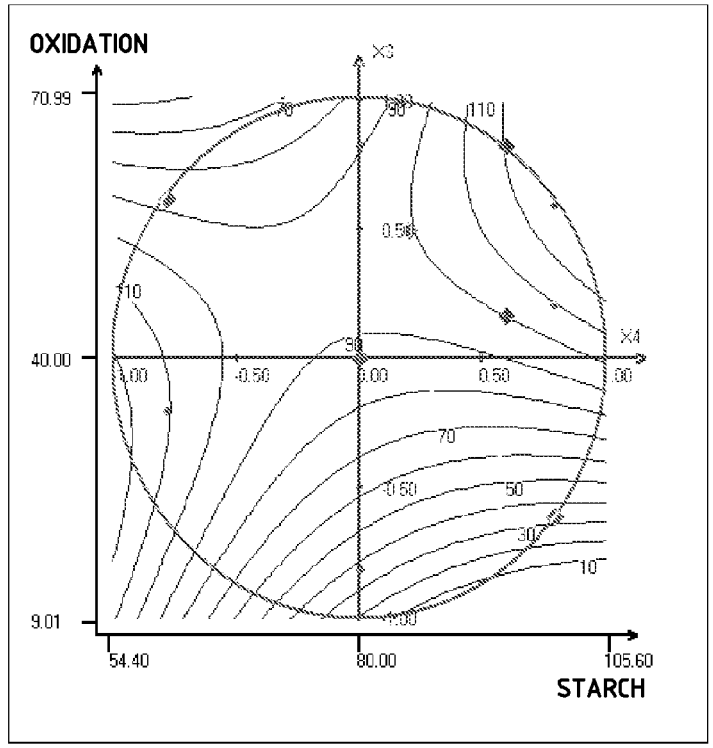
FIG. 14: Two-dimensional graphic study modelling the effects of the 4 experimental parameters (amine/starch equivalent value; pH of the reaction; level of oxidation of the starch and starch concentration in the reaction medium) on the coupling yield of cadaverine with the starch microparticles.

With regard to the second experiment plan, it was carried out so as to be able to quantitively optimise coupling and to model the response to variations of different experimental parameters on the nitrogen content of the microparticles. The second experiment plan comprised 25 experiments and was based on the use of a Doelhert matrix (Table 2). The parameters studied were the number of amine/starch equivalent value (tested at 5 levels), the pH of the reaction (tested on 7 levels), the extent of oxidation of the starch (tested at 7 levels) and, lastly, the starch concentration in the reaction medium (tested at 3 levels). As was the case for the first experiment plan, the response was evaluated, for all the experiments, by measuring the percentage of nitrogen contained in the final microparticles and the coupling yield (principle judging points by elemental analysis), as well as the granulometric distribution of the microparticles obtained (secondary judging point measured with a Coulter Multisizer™ counter). The results obtained made it possible to model the response, in terms of coupling yield, as a function of variations in the experimental parameters (FIG. 14). The circle in FIG. 14 represents, in a 2-dimensional manner, the experimental region studied during the second experiment plan. During said second experiment plan, it was possible to determine the conditions for which coupling between oxidised starch and cadaverine is at a maximum with a yield close to 100% (upper right-hand portion of the circle in FIG. 14).

All these results enabled optimisation of microparticle preparations resulting from coupling of oxidised starch and cadaverine. The experiment plans were used in order to define the ideal experimental conditions for obtaining microparticle preparations having the properties required for the desired application. Three types of formulation (formulations A, B and C), having ideal morphological characteristics for diagnostic applications in medical imaging were thus obtained from these plans.

TABLE 2

Experiment plan number 2, studying the quantitative influence of four factors - the amine/starch equivalent value (tested at five levels), the pH of the reaction (tested at seven levels), the level of oxidation of the starch (tested at seven levels) and, lastly, the starch concentration in the reaction medium (tested on three levels) - on the response by way of reaction yield and the percentage of nitrogen in the starch microparticles at the end of the coupling reaction.

| Exp no. | Equivalent | pH | Oxidation [%] | Starch] (mM/L) | Coupling yield [%] | Nitrogen [%] |
|---|---|---|---|---|---|---|
| 1 | 2.50 | 8.50 | 40.00 | 80.00 | 3.78 | 0.32 |
| 2 | 0.50 | 8.50 | 40.00 | 80.00 | 52.21 | 4.42 |
| 3 | 2.00 | 11.50 | 40.00 | 80.00 | 7.09 | 0.60 |
| 4 | 1.00 | 5.50 | 40.00 | 80.00 | 2.13 | 0.18 |
| 5 | 2.00 | 5.50 | 40.00 | 80.00 | 2.24 | 0.19 |
| 6 | 1.00 | 11.50 | 40.00 | 80.00 | 74.66 | 6.32 |
| 7 | 2.00 | 9.50 | 65.00 | 80.00 | 75.74 | 8.84 |
| 8 | 1.00 | 7.50 | 15.00 | 80.00 | 8.54 | 0.33 |
| 9 | 2.00 | 7.50 | 15.00 | 80.00 | 4.14 | 0.16 |
| 10 | 1.50 | 10.50 | 15.00 | 80.00 | 35.19 | 1.36 |
| 11 | 1.00 | 9.50 | 65.00 | 80.00 | 77.11 | 9.00 |
| 12 | 1.50 | 6.50 | 65.00 | 80.00 | 52.69 | 6.15 |
| 13 | 2.00 | 9.50 | 46.25 | 100.00 | 94.20 | 8.82 |
| 14 | 1.00 | 7.50 | 33.75 | 60.00 | 87.57 | 6.54 |
| 15 | 2.00 | 7.50 | 33.75 | 60.00 | 78.06 | 5.83 |
| 16 | 1.50 | 10.50 | 33.75 | 60.00 | 104.31 | 7.79 |
| 17 | 1.50 | 8.50 | 58.75 | 60.00 | 86.50 | 9.48 |
| 18 | 1.00 | 9.50 | 46.25 | 100.00 | 94.09 | 8.81 |
| 19 | 1.50 | 6.50 | 46.25 | 100.00 | 74.97 | 7.02 |
| 20 | 1.50 | 8.50 | 21.25 | 100.00 | 34.54 | 1.79 |
| 21 | 1.50 | 8.50 | 40.00 | 80.00 | 87.89 | 7.44 |
| 22 | 1.50 | 8.50 | 40.00 | 80.00 | 65.09 | 5.51 |
| 23 | 1.50 | 8.50 | 40.00 | 80.00 | 49.02 | 4.15 |
| 24 | 1.50 | 8.50 | 40.00 | 80.00 | 83.04 | 7.03 |
| 25 | 1.50 | 8.50 | 40.00 | 80.00 | 91.31 | 7.73 |

Preparation of Formulation A:

4 g of 50% oxidised starch, i.e. 0.022 mols of glucose units, were incubated in 120 ml water and contacted with 2268 mg cadaverine ($NH_2(CH_2)_5NH_2$) dissolved in 120 ml water. The suspension was placed under stirring for 18 hours in a dark place at a temperature of 40° C. In order to stabilise the imine formed, 420 mg of $NaBH_4$ dissolved in 10 ml water was added to the modified starch suspension under stirring for 15 minutes. The particles were then decanted, filtered and washed three times with 200 ml water, then lyophilised.

Preparation of Formulation B:

4 g of 58.75% oxidised starch, i.e. 0.022 mols of glucose units, were incubated in 120 ml water and contacted with 4048 mg cadaverine ($NH_2(CH_2)_5NH_2$) dissolved in 250 ml water, adjusting the pH of the suspension to 8.8. The suspension was placed under stirring for 18 hours in a dark place at a temperature of 40° C. In order to stabilise the imine formed, 760 mg of $NaBH_4$ dissolved in 10 ml water was added to the modified starch suspension under stirring for 60 minutes. The particles were then decanted, filtered and washed three times with 200 ml water, then lyophilised.

Preparation of Formulation C:

4 g of 65% oxidised starch, i.e. 0.022 mols of glucose units, were incubated in 120 ml water and contacted with 2920 mg cadaverine ($NH_2(CH_2)_5NH_2$) dissolved in 158 ml water, adjusting the pH of the suspension to 8.8. The suspension was placed under stirring for 18 hours in a dark place at a temperature of 40° C. In order to stabilise the imine formed, 420 mg of $NaBH_4$ dissolved in 10 ml water was added to the modified starch suspension under stirring for 60 minutes. The particles were then decanted, filtered and washed three times with 200 ml water, then lyophilised.

No. 7

Biodistribution and Metabolisation of Particles Coupled to Cadaverine

The pharmacokinetic profile of the microparticles coupled to cadavarine (formulations A, B, C of example 6) after complexation of $^{99m}$Tc and intravenous is administration was studied.

In order to do this, two types of study were carried out in healthy animals:
  dynamic and static scintigraphic studies;
  studies of the biodistribution of the starch microparticles and chromatographic separation of urinary metabolites.

a) Scintigraphic Studies

The scintigraphic studies were carried out using different ready-to-use kits containing 50 μg of SnCl$_2$ and 20 mg of microparticles of the formulations concerned A, B and C prepared in accordance with example 6. After labelling with a sodium pertechnetate ($^{99m}$TcO$_4$) solution, the radiochemical purity of the different kits was checked, with the results being greater than 95% in each case (Table 3).

Figure 15:
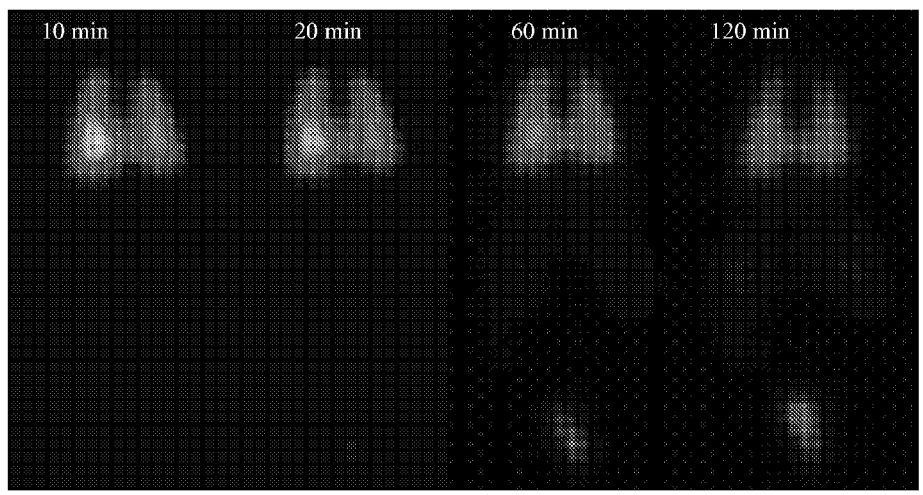
FIG. 15: Typical images taken after intravenous injection of starch microparticles labelled with $^{99m}$Tc (formulation C) in male Wistar rats. The planar images (identical windowing) were extracted at 10, 20, 60 and 120 minutes of a dynamic study lasting 120 minutes (180 45-second images).
Figure 16:
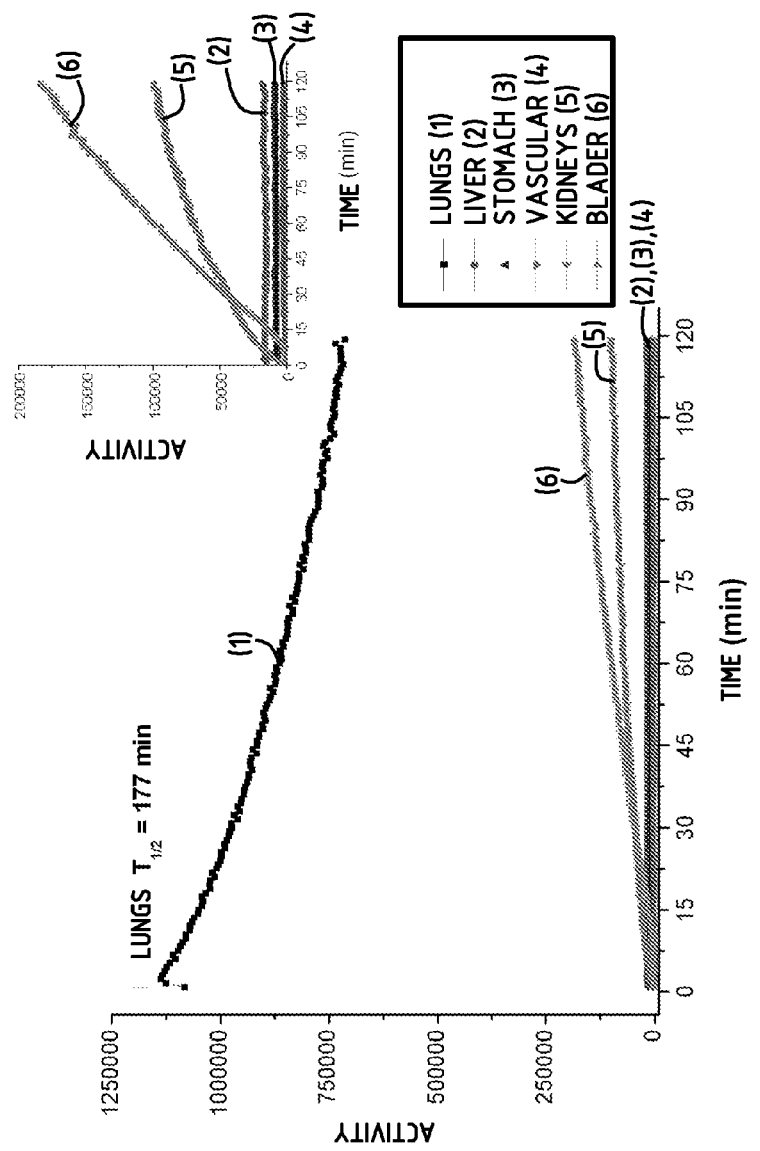
FIG. 16: Example of the time-activity curve obtained from the dynamic scintigraphic studies carried out after intravenous injection of starch microparticles labelled with $^{99m}$Tc (formulation C) in male Wistar rats.
Figure 17:
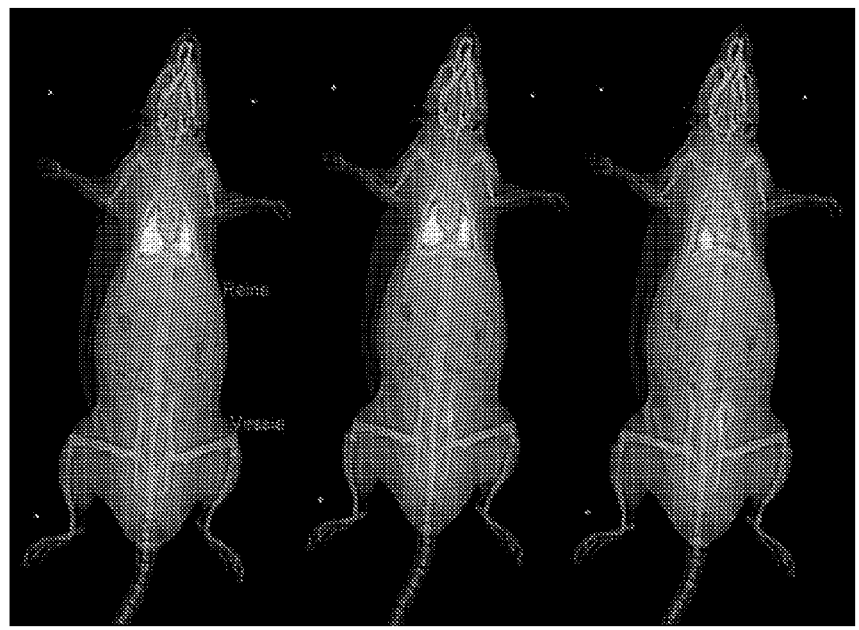
FIG. 17: Typical images taken after intravenous injection of starch microparticles labelled with $^{99m}$Tc (formulation C) in male Wistar rats. The images are the result of X-ray imaging together with a static scintigraphic acquisition (identical windowing) carried out 10, 20 and 90 minutes post-injection (600-second static).

The dynamic studies were carried out on male Wistar rats (n=3) for a duration of 120 min (FIG. 15). They made it possible to establish time-activity curves (FIG. 16), from which it was possible to obtain various activity ratios (Table 3). Scintigraphic static acquisitions together with scanner imaging were also carried out in order to anatomically trace the distribution of the tracer at different times (FIG. 17).

These various studies made it possible to observe a predominantly pulmonary localisation of the tracer after intravenous injection (FIGS. 15 and 17), with a pulmonary half-life between 1.5 and 3 hours depending on the formulation (Table 3). The time-activity curves obtained during the dynamic studies reveal a renal and urinary elimination of the tracer with profiles of hepatic, digestive and vascular activity which remain constant over time (FIG. 16).

The in vitro and in vivo characteristics of formulation C are:
Radiochemical purity (%): 98±2;
Particle size between 4 and 90 μm;
Pulmonary half-life (h): 3±0.50;
Pulmonary activity/vascular activity ratio [t=30 min]: 310±116.

These characteristics are extremely conducive to their clinical use as a radiopharmaceutical for scinitgraphic imaging of pulmonary perfusion.

b) Biodistribution Study

The biodistribution studies were carried out using ready-to-use kits containing 50 μg of SnCl$_2$ and 20 mg of microparticles of formulation C (the formulation having the most conducive scintigraphic characteristics). After labelling with a sodium pertechnetate ($^{99m}$TcO$_4$) solution, 10 MBq of a suspension of starch microparticles labelled with $^{99m}$Tc were injected intravenously into male Wistar rats (n=8). At 15 and 120 minutes post-injection, the animals were killed (n=4 for each time point), and their organs were removed, washed, weighed and countered with a gamma counter. The results confirmed pulmonary distribution of the tracer, since more than 80% of the injected activity was found in the lungs (Table 4). This pulmonary activity was relatively stable, since after 120 minutes, 70% of the activity injected was still present in the lungs. The elimination of the tracer, as revealed during scintigraphic studies, was principally urinary.

TABLE 3

In vitro and in vivo characteristics of three different ready-to-use kits containing 50 μg of SnCL$_2$ and 20 mg of microparticles of the formulations concerned (A, B and C).

| Kit | Bio-chemical purity [%] | Size [μm] | % Particles <10 μm | Pulmonary half-life [h] | Lung/vascular activity [t = 30 min] | Lung/liver activity [t = 30 min] |
|---|---|---|---|---|---|---|
| Formulation A | 96 ± 1 | 5-80 | 17 ± 1 | 1.4 ± 0.17 | 84 ± 44 | 100 ± 63 |
| Formulation B | 98 ± 1 | 5-70 | 33 ± 7 | 1.4 ± 0.25 | 133 ± 18 | 94 ± 12 |
| Formulation C | 98 ± 2 | 5-90 | 30 ± 3 | 3 ± 0.50 | 310 ± 116 | 99 ± 34 |

TABLE 4

Study of biodistribution of starch microparticles labelled with $^{99m}$Tc (formulation C) 15 and 120 minutes after intravenous injection in male Wistar rats (n = 4 for each time point).

| Formulation C | % D.I. [15 min] | % D.I./g organ [15 min] | % D.I. [120 min] | % D.I./g organ [120 min] |
|---|---|---|---|---|
| Blood | 2.08 ± 0.27 | 0.13 ± 0.02 | 1.83 ± 0.27 | 0.11 ± 0.01 |
| Lungs | 83.36 ± 2.54 | 70.25 ± 7.67 | 70.01 ± 1.07 | 54.66 ± 7.34 |
| Liver | 2.44 ± 0.23 | 0.22 ± 0.05 | 2.44 ± 0.51 | 0.23 ± 0.06 |
| Heart | 0.26 ± 0.12 | 0.31 ± 0.16 | 0.12 ± 0.04 | 0.15 ± 0.04 |
| Spleen | 0.15 ± 0.04 | 0.23 ± 0.04 | 0.24 ± 0.04 | 0.32 ± 0.05 |
| Kidneys | 3.51 ± 0.16 | 1.63 ± 0.20 | 15.59 ± 1.19 | 6.98 ± 0.88 |
| Bladder | 1.74 ± 1.24 | 8.40 ± 6.89 | 1.72 ± 0.25 | 3.67 ± 2.57 |
| Brain | 0.05 ± 0.01 | 0.03 ± 0.00 | 0.04 ± 0.01 | 0.03 ± 0.01 |
| Stomach | 0.33 ± 0.13 | 0.10 ± 0.04 | 0.86 ± 0.13 | 0.16 ± 0.10 |

TABLE 4-continued

Study of biodistribution of starch microparticles labelled with
$^{99m}$Tc (formulation C) 15 and 120 minutes after intravenous injection
in male Wistar rats (n = 4 for each time point).

| Formulation C | % D.I. [15 min] | % D.I./ g organ [15 min] | % D.I. [120 min] | % D.I./ g organ [120 min] |
|---|---|---|---|---|
| Intestines | 0.82 ± 0.20 | 0.04 ± 0.01 | 3.46 ± 0.73 | 0.16 ± 0.03 |
| Carcass | 5.30 ± 0.92 | 0.04 ± 0.01 | 3.50 ± 0.40 | 0.03 ± 0.00 |

The results are expressed as a percentage of the dose injected (% D.I.) and as a percentage of the dose injected per gram of organ (% D.I./g organ).

In order to complete these biodistribution results, a study by way of chromatographic separation of the urinary metabolites was carried out. After intravenous injection of starch microparticles (formulation C) labelled with $^{99m}$Tc in male Wistar rats (n=2), the animals were placed inside metabolism cages which allowed urine to be collected during the twelve hours following administration of the tracer.

Figure 18:
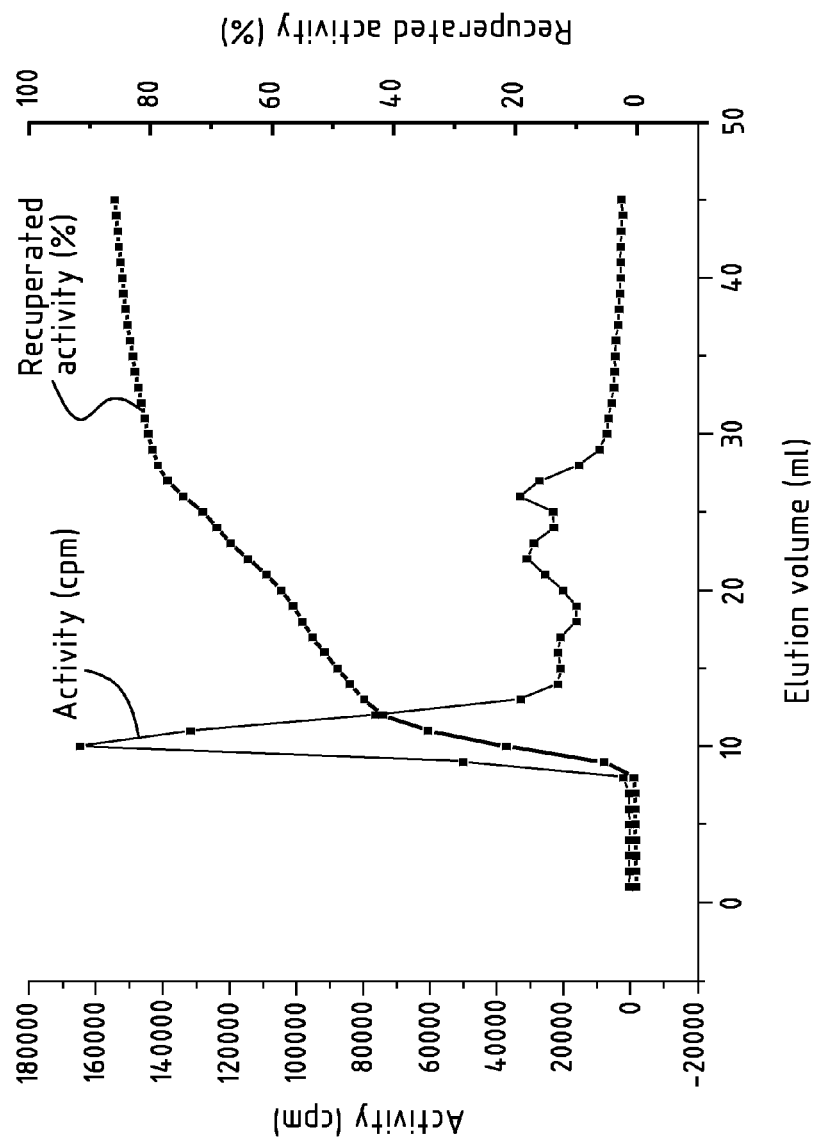
FIGS. 18, 19 and 20: Separation by means of gel permeation chromatography of urinary metabolites collected after intravenous injection of male Wistar rats with starch microparticles labelled with $^{99m}$Tc (formulation C).
Figure 19:
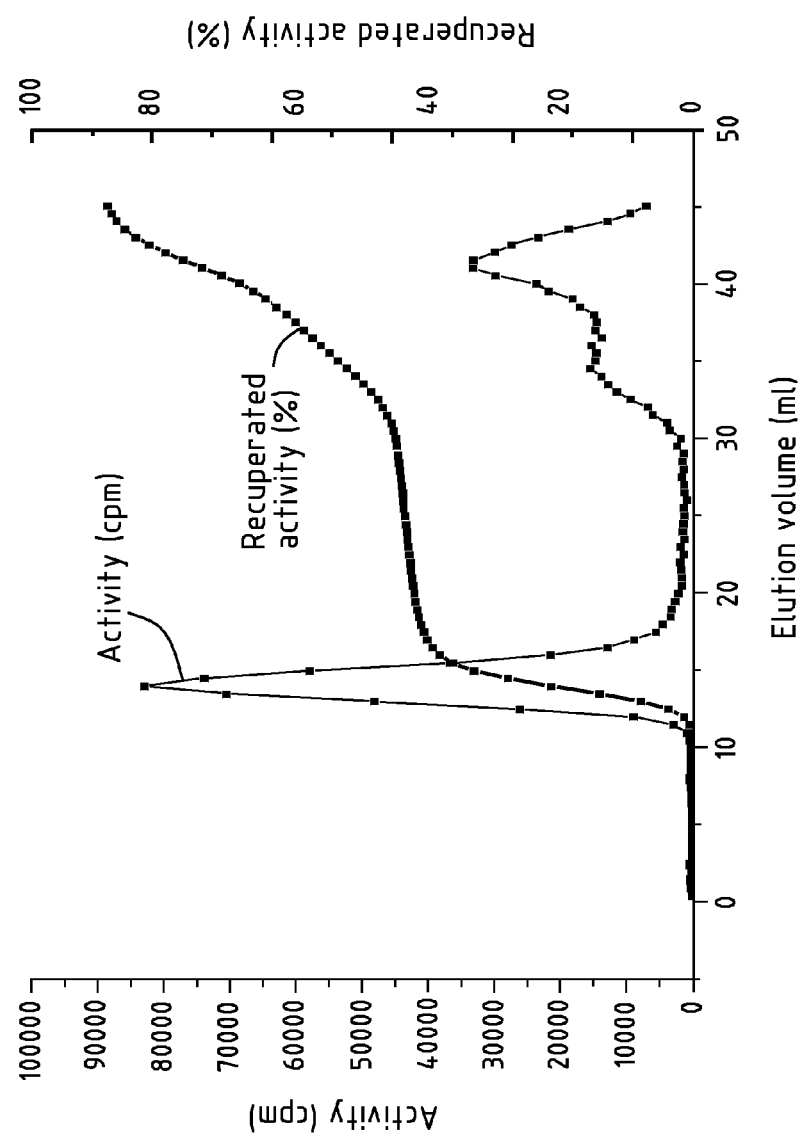
Figure 20:
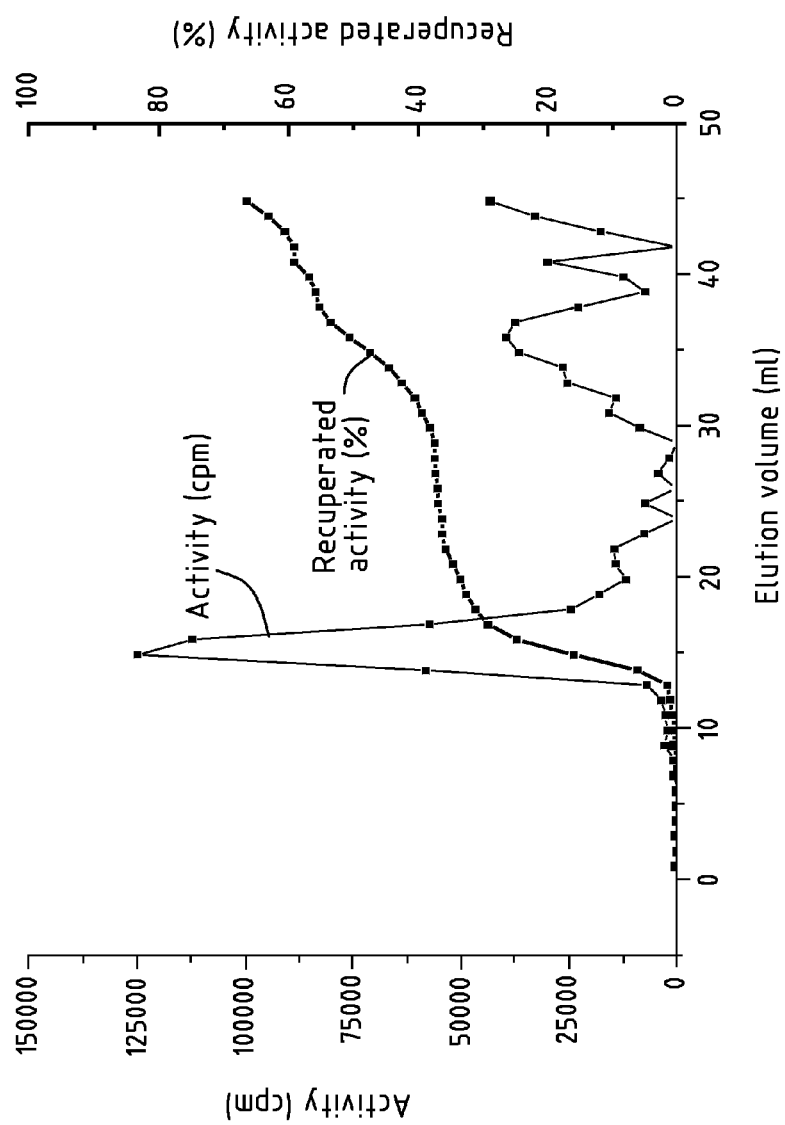

Various urinary samples were thus able to be eluted using gel permeation columns of varying porosity (Sephadex G15, P6 and Sephadex G50) which made it possible to obtain a first characterisation of the molecular distribution of the radio labelled urinary metabolites (FIGS. 18, 19 and 20). Elution using a Sephadex G15 column with an exclusion limit of 1,500 daltons (FIG. 18) revealed a molecular distribution greater than the exclusion limit for almost 50% of the urinary metabolites. Elution using a P6 column with an exclusion limit of 5,000 daltons (FIG. 19) revealed a molecular distribution greater than the exclusion limit for almost 40% to 50% of the urinary metabolites. Lastly, elution using a Sephadex G50 column with an exclusion limit of 10,000 daltons (20) revealed a molecular distribution greater than the exclusion limit for almost 30 to 40% of the urinary metabolites. In conclusion, gel permeation chromatography contributes information regarding the approximately molecular distribution of urinary metabolites, approximately 50% of said distribution being formed of molecules smaller than 1,500 daltons (corresponding to 8 glucose units), approximately 10% of molecules between 1,500 and 5,000 daltons in size (between 8 and 27 glucose units), approximately 10% of molecules between 5,000 and 10,000 daltons in size (between 27 and 55 glucose units) and, lastly, approximately 30% of molecules larger than 10,000 daltons.

All the scintigraphic and biodistribution studies carried out with modified starch microparticles labelled with $^{99m}$Tc reveal biological performances which are compatible with in vivo use of the radiopharmaceutical. The characteristics of controlled release and homogeneity of $^{99m}$Tc from its pulmonary reservoir after intravenous injection are the result of the combination of:
 a particularly homogenous size and morphology;
 good control of the chemistry for coupling the complexing agent;
 the choice of an effective complexing agent with regard to retaining the radiotracer $^{99m}$Tc.

REFERENCES

Häfeli, U O 2001, Radioactive Microspheres For Medical Applications. In: Bulte J, de Kuyper M (eds) Focus on biotechnology. Kluwer Academic Publishing
Häfeli U O, Casillas S, Dietz D W, Pauer G J, Rybicki L A, Conzone S D, Day D E, Hepatic Tumor Radioembolization in a Rat Model Using 186/188 Radioactive Rhenium Glass Microspheres, Int. J. Radiation Oncology Biol. Phys., Vol. 44, No. 1, pp. 189-199, 1999
Delgado H A, Diaz Acevedo R V, Evora Garcia C M, Mallol E J, Soriano Torres M I, Microspheres of biodegradable synthetic polymers in the manufacture of reactive equipment for the preparation of radiopharmaceuticals. Patent ES 2096521, 1997.
Delgado A, Soriano I, Sanchez E, Oliva M, Evora C, Radiolabelled biodegradable microspheres for lung imaging. Eur J Pharm Biopharm. 2000 September; 50(2):227-36
Kellaway I W, Seale L, Spencer P S. The in vitro characterization and biostability of $^{99m}$Tc-dextran and its accumulation within the inflammed paws of adjuvant-induced arthritic rats. Pharm Res. 1995 April; 12(4):588-93
Akgun A, Tani Acar E, Taner M S, Ozcan Z, Ok E. Scintigraphic diagnosis of protein-losing enteropathy secondary to amyloidosis. Turk J Gastroenterol. 2005 March; 16(1): 41-3
Paiva G R, Filho R S, Ferreira L M, Wagner J, Nogueira S A, Novo N F, Juliano Y, Rocha J L. Phytate technetium-$^{99m}$ versus dextran 500 technetium-$^{99m}$ in the sentinel lymph node biopsy. Acta Radiol. 2006 February; 47(1):65-70
Andersson A, Capala J, Carlsson J. Effects of EGF-dextran-tyrosine-$^{131}$I conjugates on the clonogenic survival of cultured glioma cells. J Neurooncol. 1992 November; 14(3): 213-23
Line B R, Weber P B, Lukasiewicz R, Dansereau R N. Reduction of background activity through radiolabeling of antifibrin Fab' with $^{99m}$Tc-dextran. J Nucl Med. 2000 July; 41(7):1264-70.

What is claimed is:
1. A process for preparing a composition comprising polysaccharide particles having one or more complexing groups obtained by covalently bonding putrescine NH$_2$ (CH$_2$)$_4$ NH$_2$, spermine H$_2$N(CH$_2$)$_3$NH(CH$_2$)$_4$NH(CH$_2$)$_3$ NH$_2$, spermidine NH$_2$(CH$_2$)$_3$NH(CH$_2$)$_4$NH$_2$, or cadaverine NH$_2$(CH$_2$)$_5$ NH$_2$ with particles of non-crosslinked polysaccharide, all or some of said complexing groups forming a complex with at least one polyvalent metal selected from the group of radioactive isotopes consisting of technetium, rhenium, copper, strontium, indium, samarium, tin, scandium, yttrium, gallium, gadolinium and lutetium, wherein the polysaccharide is starch,
 said process comprising the steps of:
  i) bringing the particles of non-crosslinked polysaccharide into contact with a controlled oxidizing agent;
  ii) bringing the oxidised polysaccharide particles into contact with a complexing compound selected from amongst putrescine, spermine, spermidine or cadaverine;
  iii) optionally bringing the polysaccharide particles obtained in step ii) into contact with a reducing agent; and iv) bringing the polysaccharide particles obtained in step ii) or step iii) into contact with a polyvalent metal salt.

2. The process according to claim 1, wherein the polyvalent metal is $^{99m}$Tc.

3. The process according to claim 1, wherein step iv) is carried out in the presence of reducing agents of the tin, borate and derivatives or ascorbic acid type.

4. A composition comprising polysaccharide particles having one or more complexing groups obtained by covalently bonding putrescine $NH_2(CH_2)_4NH_2$, spermine $H_2N(CH_2)_3NH(CH_2)_4NH(CH_2)_3NH_2$, spermidine $NH_2(CH_2)_3NH(CH_2)_4NH_2$, or cadaverine $NH_2(CH_2)_5NH_2$ with particles of non-crosslinked polysaccharide, all or some of said complexing groups forming a complex with at least one polyvalent metal selected from the group of radioactive isotopes consisting of technetium, rhenium, copper, strontium, indium, samarium, tin, scandium, yttrium, gallium, gadolinium and lutetium, wherein the polysaccharide is starch,
said composition being obtained by a process comprising the steps of:
   i) bringing the particles of non-crosslinked polysaccharide into contact with a controlled oxidizing agent;
   ii) bringing the oxidised polysaccharide particles into contact with a complexing compound selected from amongst putrescine, spermine, spermidine or cadaverine; and
   iii) bringing the polysaccharide particles obtained in step ii) into contact with a polyvalent metal salt.

5. The composition according to claim 4, wherein the particle size is between 10 nm and 200 μm.

6. The composition according to claim 4, wherein the polysaccharide is of a vegetable or microbiological origin.

7. The composition according to claim 4 further comprising a pharmaceutically acceptable excipient.

8. A diagnostic or pharmaceutical composition for the human or animal pharmacopoeia comprising a composition according to claim 4.

9. A method of medical or veterinary imaging, which method comprises administering to a subject a composition according to claim 4 and imaging the subject.

10. The method of claim 9 wherein the medical or veterinary imaging is scintigraphic imaging.

11. The method of claim 10 for the scintigraphic diagnosis of a pulmonary embolism.

12. The method of claim 10 for detecting sentinel nodes or for lymphoscintigraphy.

13. A method for visualizing one or more organs in a patient or an animal by means of medical imaging, which method comprises administering to a subject a composition according to claim 4 and imaging the subject.

14. The method of claim 13, wherein the imaged organ is a lung, the liver, the spleen, bone marrow or lymph nodes.

15. A method of treatment of cancer in a patient or an animal by means of internal radiotherapy, which method comprises administering to a subject a composition according to claim 4.

16. The method of claim 15 for treating lymph nodes or hepatic or splenic tumours.

17. The composition according to claim 4 wherein the polyvalent metal is $^{99m}$Tc.

18. The composition according to claim 4, wherein the controlled oxidizing agent is periodate.

19. The composition according to claim 18, wherein the periodate is sodium periodate.

20. The composition according to claim 4, wherein the polysaccharide is oxidized at a level ranging from 15% to 65%.

21. The composition according to claim 4, wherein the polysaccharide is oxidized at a level of about 65%.

22. A composition comprising polysaccharide particles having one or more complexing groups obtained by covalently bonding putrescine $NH_2(CH_2)_4NH_2$, spermine $H_2N(CH_2)_3NH(CH_2)_4NH(CH_2)_3NH_2$, spermidine $NH_2(CH_2)_3NH(CH_2)_4NH_2$, or cadaverine $NH_2(CH_2)_5NH_2$ with particles of non-crosslinked natural origin polysaccharide, all or some of said complexing groups forming a complex with at least one polyvalent metal selected from the group of radioactive isotopes consisting of technetium, rhenium, copper, strontium, indium, samarium, tin, scandium, yttrium, gallium, gadolinium and lutetium, wherein the polysaccharide is starch,
said composition being obtained by a process comprising the steps of:
   i) bringing the particles of non-crosslinked polysaccharide into contact with a controlled oxidizing agent;
   ii) bringing the oxidised polysaccharide particles into contact with a complexing compound selected from amongst putrescine, spermine, spermidine or cadaverine;
   iii) bringing the polysaccharide particles obtained in step ii) into contact with a reducing agent; and
   iv) bringing the polysaccharide particles obtained in step iii) into contact with a polyvalent metal salt.

23. The composition according to claim 22, wherein the particle size is between 10 nm and 200 μm.

24. The composition according to claim 22, wherein the polysaccharide is of a vegetable or microbiological origin.

25. The composition according to claim 22, wherein the controlled oxidizing agent is periodate.

26. The composition according to claim 25, wherein the periodate is sodium periodate.

27. The composition according to claim 22, wherein the polysaccharide is oxidized at a level ranging from 15% to 65%.

28. The composition according to claim 22, wherein the polysaccharide is oxidized at a level of about 65%.

29. The composition according to claim 22, wherein the polyvalent metal is $^{99m}$Tc.

30. The composition according to claim 22, further comprising a pharmaceutically acceptable excipient.

31. A diagnostic or pharmaceutical composition for the human or animal pharmacopoeia comprising a composition according to claim 22.

32. The composition according to claim 4, wherein the complexing compound is cadaverine $NH_2(CH_2)_5NH_2$.

33. The composition according to claim 22, wherein the complexing compound is cadaverine $NH_2(CH_2)_5NH_2$.

34. The diagnostic or pharmaceutical composition according to claim 8, wherein the composition comprises polysaccharide particles having a size between 10 and 100 μm for use in capillary blocking.

35. The diagnostic or pharmaceutical composition according to claim 8, wherein the composition comprises polysaccharide particles having a size between 10 and 100 μm for use in pulmonary perfusion scintigraphy.

36. The diagnostic or pharmaceutical composition according to claim 31, wherein the composition comprises polysaccharide particles having a size between 10 nm and 500 nm for use to detect or visualize sentinel ganglions.

37. The diagnostic or pharmaceutical composition according to claim 31, wherein the composition comprises polysaccharide particles having a size between 10 and 500 nm for use in lymphoscintigraphy.

38. A composition comprising polysaccharide particles and having one or more complexing groups obtained by covalently bonding putrescine $NH_2(CH_2)_4NH_2$, spermine $H_2N(CH_2)_3NH(CH_2)_4NH(CH_2)_3NH_2$, spermidine $NH_2(CH_2)_3NH(CH_2)_4NH_2$, or cadaverine $NH_2(CH_2)_5NH_2$ with particles of non-crosslinked, oxidized starch and derivatives thereof.

39. The composition according to claim 38, wherein the complexing compound is cadaverine $NH_2(CH_2)_5NH_2$.

40. A composition comprising polysaccharide particles, having one or more complexing groups obtained by covalently bonding putrescine $NH_2(CH_2)_4NH_2$, spermine $H_2N(CH_2)_3NH(CH_2)_4NH(CH_2)_3NH_2$, spermidine $NH_2(CH_2)_3NH(CH_2)_4NH_2$, or cadaverine $NH_2(CH_2)_5NH_2$ with particles of non-crosslinked oxidized polysaccharide, all or some of said complexing groups forming a complex with at least one polyvalent metal selected from the group of radioactive isotopes consisting of technetium, rhenium, copper, strontium, indium, samarium, tin, scandium, yttrium, gallium, gadolinium and lutetium, wherein the polysaccharide is starch.

41. The composition according to claim 40, wherein the complexing compound is cadaverine $NH_2(CH_2)_5NH_2$.

42. The composition according to claim 40, wherein the polyvalent metal is $^{99m}Tc$.

* * * * *